(12) United States Patent
Reinard et al.

(10) Patent No.: US 10,188,482 B2
(45) Date of Patent: Jan. 29, 2019

(54) CLEANING DEVICE FOR ENTERAL FEEDING CONNECTION

(71) Applicants: Jane Marie Reinard, Kintnersville, PA (US); Martin Von Dyck, Doylestown, PA (US)

(72) Inventors: Jane Marie Reinard, Kintnersville, PA (US); Martin Von Dyck, Doylestown, PA (US)

( * ) Notice: Subject to any disclaimer, the term of this patent is extended or adjusted under 35 U.S.C. 154(b) by 238 days.

(21) Appl. No.: 15/236,074

(22) Filed: Aug. 12, 2016

(65) Prior Publication Data

US 2017/0042637 A1 Feb. 16, 2017

Related U.S. Application Data

(60) Provisional application No. 62/204,787, filed on Aug. 13, 2015.

(51) Int. Cl.
  *A61B 90/70* (2016.01)
  *A61J 15/00* (2006.01)
  *A61M 39/16* (2006.01)

(52) U.S. Cl.
  CPC ........... *A61B 90/70* (2016.02); *A61J 15/0026* (2013.01); *A61M 39/16* (2013.01); *A61B 2090/701* (2016.02)

(58) Field of Classification Search
  CPC ............... A61B 90/70; A61B 2090/701; A61J 15/0026; A61M 39/16

USPC ........................................................ 15/160
See application file for complete search history.

(56) References Cited

U.S. PATENT DOCUMENTS

| | | | | |
|---|---|---|---|---|
| 6,187,104 B1* | 2/2001 | Bozarjian | ............ | A46B 17/02 134/6 |
| 7,526,830 B2* | 5/2009 | Forrest | ...................... | B08B 1/00 15/209.1 |
| 8,172,825 B2* | 5/2012 | Solomon | ............. | A61M 39/162 604/256 |
| 8,777,504 B2* | 7/2014 | Shaw | .................... | A61M 39/16 15/104.93 |
| 2001/0016962 A1* | 8/2001 | Moore | ...................... | B08B 9/00 15/104.16 |
| 2008/0052845 A1* | 3/2008 | Djang | .................. | A46B 5/0012 15/23 |
| 2010/0197817 A1* | 8/2010 | Bui | .......................... | A61L 27/34 521/53 |
| 2011/0094599 A1* | 4/2011 | Meyer | .................... | A61B 1/126 137/15.04 |
| 2012/0144608 A1* | 6/2012 | Berry | ..................... | A61B 90/70 15/104.05 |
| 2016/0214142 A1 | 7/2016 | Davis | | |

* cited by examiner

*Primary Examiner* — Weilun Lo
(74) *Attorney, Agent, or Firm* — Dunlap Bennett & Ludwig PLLC; Brendan E. Squire

(57) ABSTRACT

A cleaning device for cleaning a connection end of an enteral feeding system. The device has a handle, and a plurality of cleaning elements disposed to clean the internal surfaces of the enteral feeding connector. A centering post facilitates insertion of the cleaning device in the connection end, and seals the enteral feeding channel from the entry of contaminants during cleaning.

10 Claims, 4 Drawing Sheets

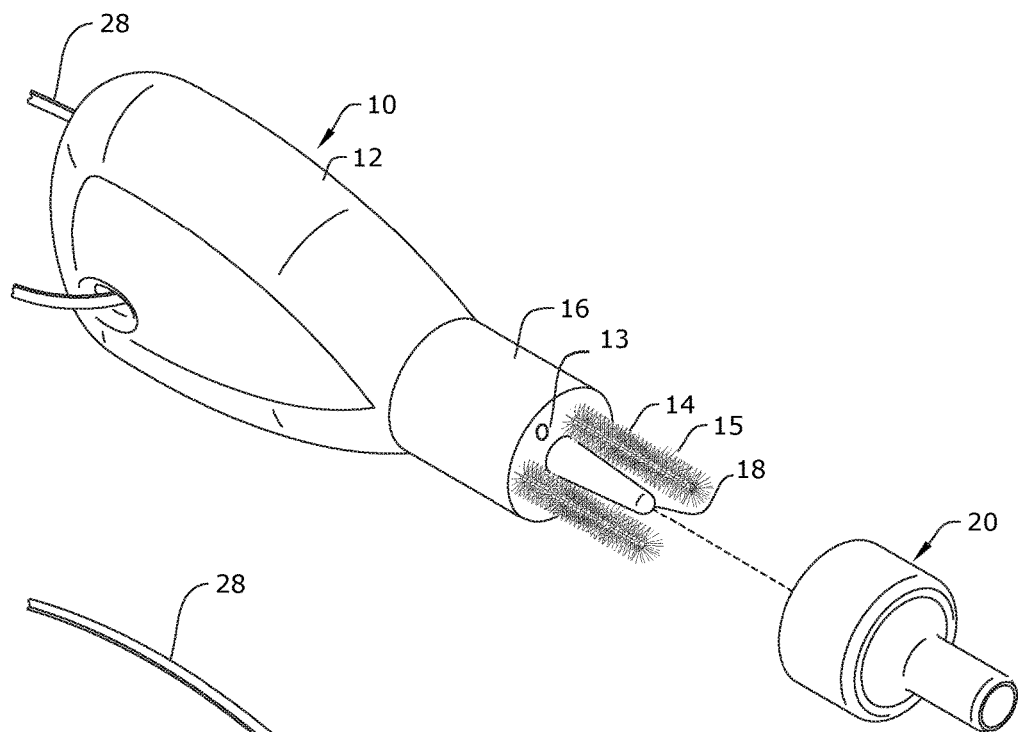
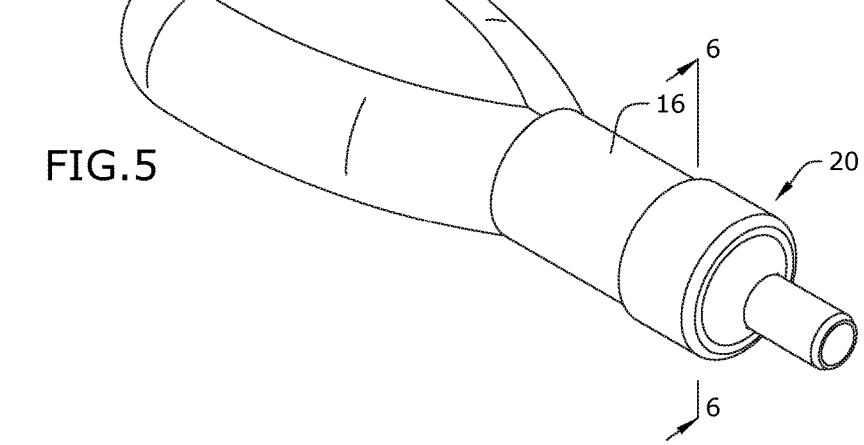
FIG.4
FIG.5

CLEANING DEVICE FOR ENTERAL FEEDING CONNECTION

CROSS-REFERENCE TO RELATED APPLICATION

This application claims the benefit of priority of U.S. provisional application No. 62/204,787, filed Aug. 13, 2015, the contents of which are herein incorporated by reference.

BACKGROUND OF THE INVENTION

The present invention relates to connectors for enteral feeding systems, and more particularly to apparatus and methods for cleaning the same.

A new and unique international standard (ISO Standard 80369-3) has been designed to promote better patient safety and helps ensure connectors for other medical delivery systems are not compatible with enteral feeding tubes. This will reduce the frequency of medical tubing misconnections. Use of these new ENFit® Connectors, has been predicted to result in ENFit® enteral formula and other catheter contents to accumulate in the internal threads and internal architecture of the enteral feeding connector. These complex internal architectural features of the enteral connector and subsequent organic debris risks promoting bacteria growth by its complicated design, with difficult to access internal architectural features cleaning the enteral connector will be very difficult.

As can be seen, there is a need for a system and method for a cleaning device available to address the unique cleaning challenges of the Enteral Connector.

SUMMARY OF THE INVENTION

In one aspect of the present invention a cleaning device according to embodiments of the invention includes: a handle having a proximal end and a distal end; a cleaning fitment attached to the distal end; and a plurality of cleaning elements extending from the fitment disposed in a spaced apart relation and extending along a longitudinal axis of the device. In some embodiments, the device may also include a centering post extending from the fitment, wherein the plurality of cleaning elements are disposed about the centering post. A spring may be received within a cavity of the fitment and is configured to bias the centering post for reciprocating movement within the fitment.

In some embodiments, the cleaning elements comprise a plurality of brushes. The brushes may include a plurality of bristles extending laterally outwardly along a length of a brush form element. The bristles may also be configured to extend longitudinally from a tip end of the brush form element. The cleaning element may include one of a cotton or foam swab. The cleaning element may alternatively include a woven fabric.

In certain aspects of the invention, the handle is formed of an anti-microbial material. The cleaning element may also be formed of an anti-microbial material. A tether may be attached to the proximal end of the handle. In yet other aspects of the invention, the handle may also include a reservoir configured to contain a cleaning solution. The handle may also be compressible to deliver a quantity of the cleaning solution to the cleaning element via a channel formed through the cleaning element.

These and other features, aspects and advantages of the present invention will become better understood with reference to the following drawings, description and claims.

BRIEF DESCRIPTION OF THE DRAWINGS

FIG. 4 is a perspective view of the cleaning device aligned with a connector of an enteral feeding system.

FIG. 5 is a perspective view of the cleaning device operatively coupled to the enteral connector for cleaning.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides an apparatus and method for cleaning connection couplings for enteral feeding systems. The apparatus is configured to clean the internal surface architecture of such connectors to reduce the risk of patient illness due to contaminants that may be harbored in the connections.

As stated above, a new and unique international standard (ISO Standard 80369-3) has been promulgated to promote better patient safety and helps ensure connectors for other medical delivery systems are incompatible with the connectors for feeding tubes. While this new standard will reduce the frequency of medical tubing misconnections, it also has the potential to create an additional patient hazard due to bacterial growth and contamination of these connector fittings.

Using the new connectors, such as an ENFit® connector, enteral formula will be prone to accumulate in the threads and other internal architectural surfaces of the connectors. Because enteral formulas are comprised of organic material and are primarily milk based compositions, bacterial growth, due to formula accumulation within the connection presents a potential patient contamination hazard. The complex internal architecture of the enteral formula connectors makes conventional cleaning methods inadequate, thus cleaning of these connectors will be very difficult. The invention claimed here solves this problem. Handle 12 per claim 1 that is made using materials containing antimicrobial molecular entities that will help reduce germs from growing on the device.

Figure 1:
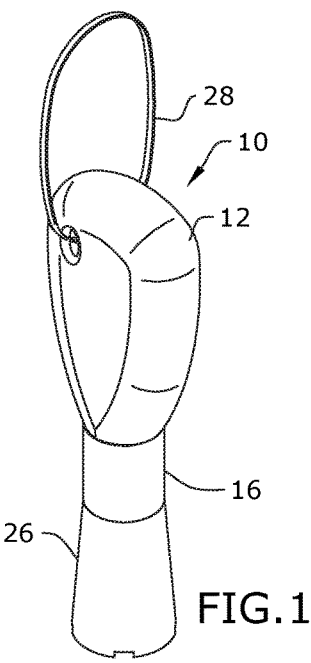
FIG. 1 is a perspective view of an embodiment of a cleaning device with protective cap according to aspects of the invention.
Figure 2:
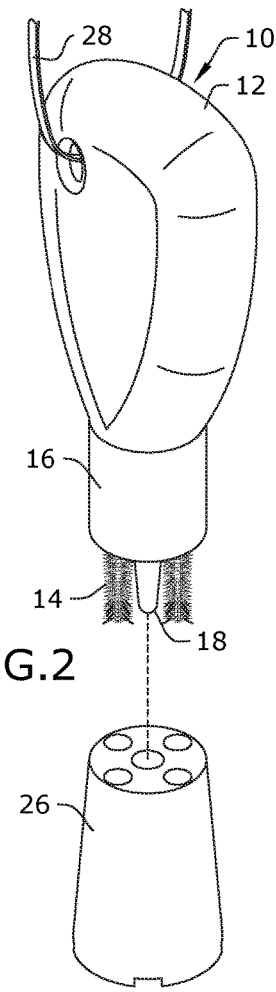
FIG. 2 is an exploded view of the embodiment of the cleaning device.
Figure 3:
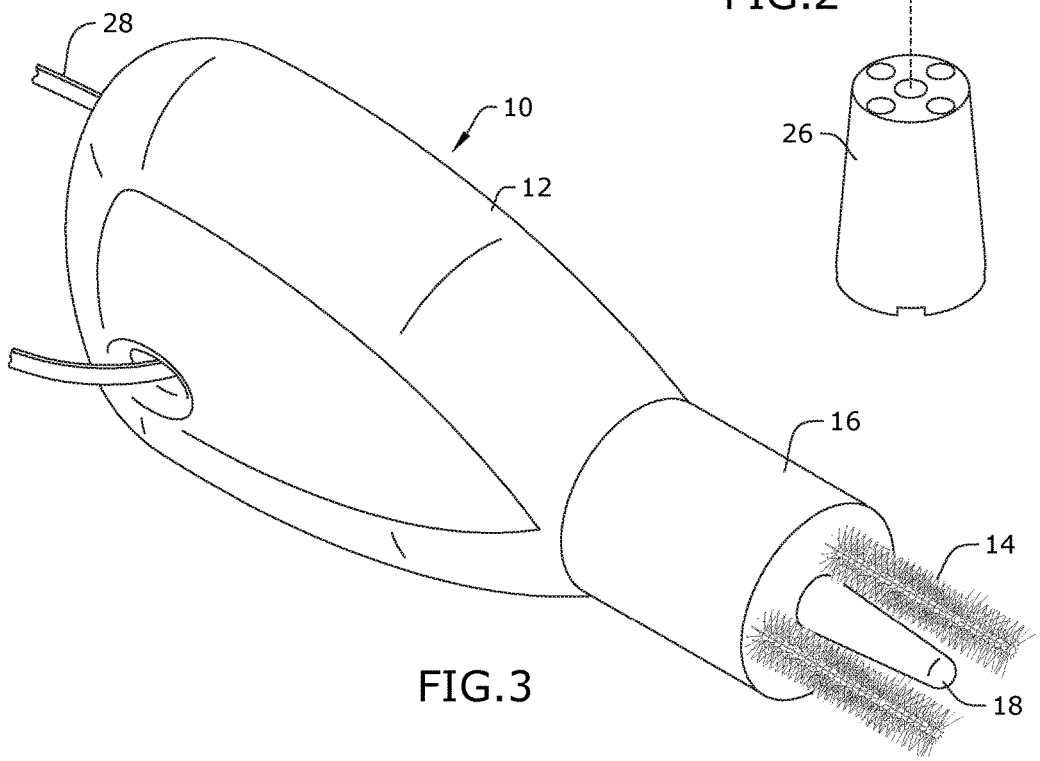
FIG. 3 is a perspective view of the cleaning device with a protective cap removed.
Figure 6:
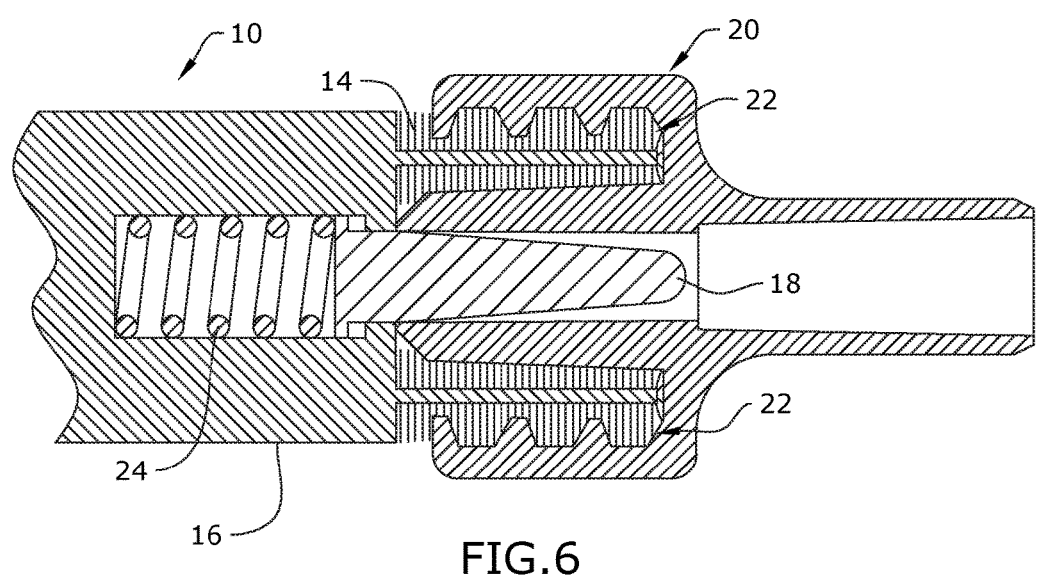
FIG. 6 is a detail sectional view along line 6-6 of FIG. 5.
Figure 7:
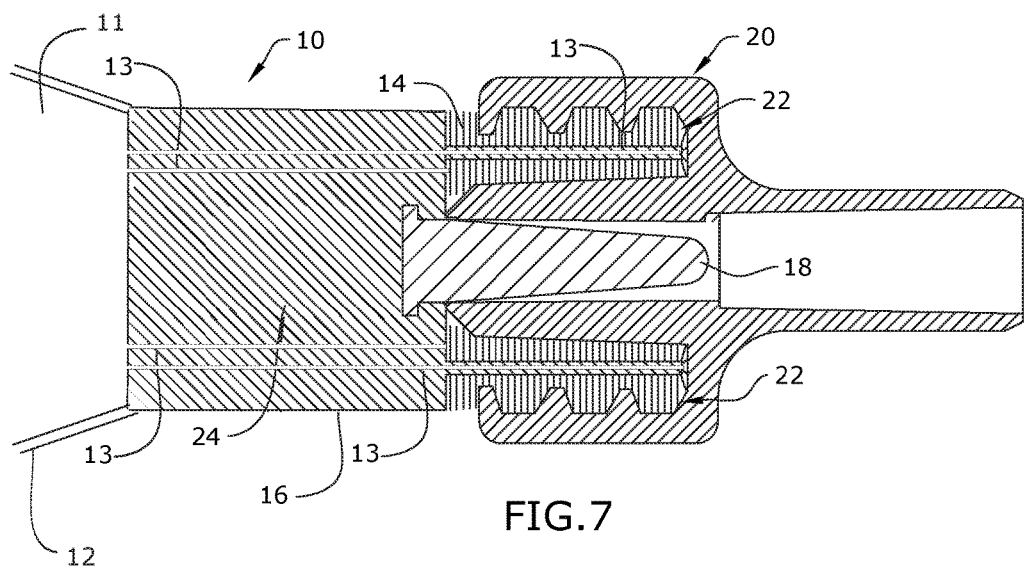
FIG. 7 is a detail sectional view of an alternate embodiment taken along line 6-6 of FIG. 5.

As seen in reference to FIGS. 1-3, an embodiment of a cleaning device 10 according to aspects of the present invention are shown. The cleaning device 10 includes a handle 12 with a cleaning fitment 16 attached to a distal end that is configured to clean the internal architectural surfaces of an enteral feeding connector 20, seen in reference to FIG. 4-6. Such connectors 20 are configured to interconnect a Nasogastric, a Jejunal, a percutaneous endoscopic gastronomy (PEG), gastrostomy and other feeding catheters with a source of an enteral nutrition composition.

The cleaning device 10 includes a plurality of cleaning elements 14, such as brushes, that extend longitudinally from the fitment 16 at the distal end of the handle 12. The cleaning element 14 may be coupled to a shaft that is attached to the distal end of the handle 12. The cleaning element 14 may be replaceable, such that the shaft may be removably attached to the handle 12 fitment 16. The cleaning element 14 may be formed as one or more of a brush, a swab, a fabric patch. The cleaning element may be manufactured of materials containing antimicrobial molecular entities that will help prevent the growth of germs on the cleaning element 14. Similarly, the handle 12 may also be made using materials containing antimicrobial molecular entities that will help reduce the ability of germs from growing on the device.

As shown in FIGS. 2-4, the cleaning element 14, may be configured as a brush that is formed by a plurality of bristles radially disposed about a brush form element 15. The brush form element 15 may be received or formed in the distal end 16 of the handle 12. The brushes 14 are disposed in a spaced apart relation, preferably in an evenly spaced pattern that may be inscribed by a circle having a diameter that is less than or equal to an internal diameter of the enteral feeding connector 20.

Preferably, brushes 14 are formed such that the bristles are laterally disposed along a length of the brush 14 and longitudinally disposed proximal to the tip of the brush 14 so as to make effective cleaning contact with the interior screw threads and internal surfaces of the enteral feeding connector 20. This will allow for efficient cleaning of the internal architecture of the connector 20 via a twisting or rotating action by the user. In certain preferred embodiments, there are at least four cleaning elements 14 such that the user need only twist the device 10 a quarter turn before the area of the connector 20 that is cleaned by a first cleaning element 14 is overlapped by cleaning contact with a second cleaning element 14. This facilitates effective cleaning contact with the internal surface of the feeding connector, with only a 90 degree turn of the wrist.

The cleaning element 14 may alternatively be configured with a plurality of fabric swabs, such as cotton or foam swabs that are configured to enter the internal screw threads and internal surfaces of the enteral feeding connector 20. The swabs may be compressible to allow for insertion into the connection end of the enteral feeding connector 20 and then resiliently expand to make effective cleaning contact with the interior screw threads and internal architecture of the enteral feeding connector 20. This will allow for efficient cleaning of the internal architecture of the enteral feeding connector 20 via a twisting action (Clockwise or counter clockwise) by the user.

The cleaning elements 14 may alternatively be formed of a woven fabric, such as felt, that is configured to be received in the internal screw thread and internal architecture of the enteral feeding connector 20. The woven fabric may also be compressible and/or malleable to allow for insertion into the connector 20 and expand internally to make cleaning contact with the interior screw threads and internal architecture of the enteral feeding connector 20. This will allow for efficient cleaning of the internal surfaces of the enteral feeding connector 20 via a twisting action (Clockwise or counter clockwise) by the user.

The cleaning element 14 may alternatively be formed from one or more of an elastic or flexible polymer material that is dimensioned to be received in the connector 20 cavity to clean the internal screw thread and internal architecture of the enteral feeding connector 20. The flexible and malleable polymer material should be selected so that it is sufficiently flexible to allow for insertion into the enteral feeding connector 20 and make effective cleaning contact with the interior surfaces of the enteral feeding connector 20.

The cleaning device 10 of the present invention can be used dry and/or with one or more of water, a cleaning solution, with or without anti-microbial or anti-bacterial additives, or any other acceptable cleaning fluid.

In certain embodiments, the cleaning device 10 may also be configured with a centering post 18. The centering post 18 may have a tapered distal end that is dimensioned to be received within a fluid pathway for the connector 20 and enteral feeding tube coupled to the connector 20. Preferably, the centering post 18 is formed of a compressible polymer that will deform to temporarily plug the main fluid pathway lumen of the enteral feeding connector 20, thereby, preventing debris and cleaning fluids from entering the catheter and into the patient during the cleaning process.

The centering post 18 is preferably positioned between the plurality of cleaning elements 14, such that, when received within the fluid pathway, the plurality of cleaning elements 14 are disposed against the internal surface structures of the enteral connector 20, acting as a temporary plug to the main fluid pathway lumen of the feeding connector 20. The plug 18 is mounted to the handle 12. A spring 24 may be received within an internal cavity of the fitment 16 to allow for effective reciprocating motion of the soft compressible plug 18 while being advanced into and out of the enteral feeding connector 20. The spring 24 will assist in allowing the plug to return into the handle 12 to ease the cleaning process, yet provide a biasing force sufficient to keep the plug tip in contact with the enteral main lumen, thus maintaining a seal keeping out contaminants.

The cleaning device 10 may also include a protective cap 26 to protect the cleaning element 14 while not in use. The protective cap 26 is provided with a plurality of apertures disposed in a proximal, covering end of the protective cap. The apertures are defined with a sufficient depth so as to receive the cleaning element 14 within the apertures. When equipped with a centering post 18, the protective cap 26 will have an additional aperture dimensioned to receive the centering post 18 therein. A distal end of the protective cap 26 may be configured with a flat end surface, which permits the cleaning device 10 to be stored in an upright position with the fitment 16 in downward facing orientation.

The protective cap 26 may also include a drainage and aeration ports to facilitate drying of the cleaning elements 14. The aeration ports may, for example be extension of the apertures through the body of the cap 26 to the substantially flat face of the distal end of the cap 26.

As further seen in reference to FIG. 1 the cleaning device 10 may also include a tether 28, or strap, that is operatively secured to the handle 12 portion and will facilitate attachment to other fixtures for easy hanging storage, such as an IV Pole, an Enteral feeding Pumps, Bed Posts, and the like. The tether 28 may also be configured to be placed around a user's wrist.

In certain embodiments, the handle 12 portion may be configured with an internal cavity 11 that is filled with a cleaning fluid. More preferably, the walls of the internal cavity 11 are made of a soft, hollow polymer that, when pressed (squeezed), expels cleaning fluid to irrigate and flush away debris, via a fluid channel 13 extending through the cleaning element 14 and delivered to the enteral feeding connector 20.

A cleaning device 10, that incorporates brushes and/or other mechanisms as described in the claims, that will be flexible to allow for inserting into the Enteral feeding connector 20 and make cleaning contact with the interior screw threads and internal surfaces to allow for efficient cleaning. This will effectively remove organic contaminants and sediment.

It should be understood, of course, that the foregoing relates to exemplary embodiments of the invention and that modifications may be made without departing from the spirit and scope of the invention as set forth in the following claims.

What is claimed is:

1. A cleaning device, comprising:
   a handle having a proximal end and a distal end;
   a cleaning fitment attached to the distal end;
   a centering post formed from a compressible polymer deformable to temporarily plug a main fluid pathway lumen of an enteral feeding connector, the centering post oriented along a longitudinal length of the cleaning device and extending from a distal end of the cleaning fitment in a fixed position relative to the cleaning fitment;
   a plurality of cleaning elements extending from the fitment disposed in a spaced apart relation and extending along the longitudinal axis of the cleaning device.

2. The cleaning device of claim 1,
   wherein the plurality of cleaning elements are disposed about the centering post.

3. The cleaning device of claim 1, wherein the cleaning elements comprise a plurality of brushes radially disposed about the centering post.

4. The cleaning device of claim 3, wherein the brushes comprise a plurality of bristles extending laterally outwardly along a length of a brush form element.

5. The cleaning device of claim 4, wherein the bristles are configured to extend longitudinally from a tip end of the brush form element.

6. The cleaning device of claim 1, wherein the handle is formed of an anti-microbial material.

7. The cleaning device of claim 1, wherein the cleaning element is formed of an anti-microbial material.

8. The cleaning device of claim 1, further comprising;
   a tether attached to the proximal end of the handle.

9. The cleaning device of claim 1, wherein the handle further comprises:
   a reservoir configured to contain a cleaning solution.

10. The cleaning device of claim 9, wherein the handle is compressible to deliver a quantity of the cleaning solution to the cleaning element via a channel formed through the cleaning element.

* * * * *